United States Patent
Doerr et al.

(10) Patent No.: US 10,293,154 B2
(45) Date of Patent: May 21, 2019

(54) DEVICE HAVING A SURFACE STRUCTURE FOR INSERTION INTO THE HUMAN OR ANIMAL BODY

(71) Applicant: BIOTRONIK SE & Co. KG, Berlin (DE)

(72) Inventors: Thomas Doerr, Berlin (DE); Gernot Kolberg, Berlin (DE)

(73) Assignee: BIOTRONIK SE & Co. KG (DE)

( * ) Notice: Subject to any disclaimer, the term of this patent is extended or adjusted under 35 U.S.C. 154(b) by 113 days.

(21) Appl. No.: 15/009,922

(22) Filed: Jan. 29, 2016

(65) Prior Publication Data
US 2016/0228697 A1 Aug. 11, 2016

(30) Foreign Application Priority Data
Feb. 9, 2015 (EP) ...................... 15154319

(51) Int. Cl.
*A61F 2/00* (2006.01)
*A61N 1/05* (2006.01)
*A61N 1/375* (2006.01)

(52) U.S. Cl.
CPC .......... *A61N 1/0587* (2013.01); *A61F 2/0077* (2013.01); *A61N 1/059* (2013.01); *A61N 1/375* (2013.01); *A61F 2002/0081* (2013.01); *A61F 2210/0004* (2013.01); *A61F 2250/0004* (2013.01); *A61F 2250/0021* (2013.01)

(58) Field of Classification Search
CPC ................. A61F 2/02; A61F 2002/044; A61F 2002/045; A61F 2002/041
See application file for complete search history.

(56) References Cited

U.S. PATENT DOCUMENTS

| | | | |
|---|---|---|---|
| 5,925,074 A * | 7/1999 | Gingras | A61F 2/07 606/191 |
| 2009/0248171 A1 * | 10/2009 | Levine | A61B 17/0401 623/23.65 |
| 2011/0009801 A1 | 1/2011 | Blaeser et al. | |
| 2011/0021965 A1 | 1/2011 | Karp et al. | |
| 2012/0220917 A1 | 8/2012 | Silvestrini et al. | |
| 2013/0218262 A1 | 8/2013 | Ishii et al. | |
| 2014/0180065 A1 | 6/2014 | Garcia | |
| 2014/0277443 A1 | 9/2014 | Fleury et al. | |

* cited by examiner

*Primary Examiner* — Nadia A Mahmood
(74) *Attorney, Agent, or Firm* — Craig A. Fieschko, Esq.; DeWitt LLP

(57) ABSTRACT

A device (110) for insertion into a human or animal body has a surface (610) which at least partially bears a surface structure (140, 140'), wherein the coefficient of static friction between the surface structure (140, 140') and an interface within the body is anisotropic.

19 Claims, 8 Drawing Sheets

DEVICE HAVING A SURFACE STRUCTURE FOR INSERTION INTO THE HUMAN OR ANIMAL BODY

FIELD OF THE INVENTION

The present invention relates to a device for insertion into the human or animal body, for example a medical implant. In particular, the invention relates to the insertion of implants at implantation sites that are difficult to access.

BACKGROUND OF THE INVENTION

The insertion of implants into the human or animal body typically takes place by means of a surgical intervention. Implantation can involve different degrees of invasivity, surgical duration, and surgical difficulty for a surgeon depending on the implantation site, the type of implant, the implantation method, and the implantation tools used.

Implants are known in the prior art which have surface structures and surface coatings that serve to chemically, physically, and biologically modify the interface between implant and tissue in such a way that the implant has improved compatibility with the body. As examples, certain vascular stents have coatings which contain drugs having an anti-thrombogenic effect; certain bone implants have a bioactive surface structure, such that natural bone quickly intergrows with the implant; and certain implants have antimicrobial surface coatings which reduce the risk of infection and improve biocompatibility.

Implants are also known that have means mounted on the implant surface which prevent displacement or a shifting of the implant at the implantation site, and thus assure a fixed position for the implant. As examples, US 2012/0220917 A1 discloses an ocular implant having finger-like units which expand at the implantation site and thus fix the implant at the implantation site. US 2014/0180065 A1 discloses a radiopaque implant which has nibs on the implant body that anchor the implant at the implantation site.

As operative invasivity, surgery duration, and surgery difficulty increase, so do patient health risks and direct and indirect implantation costs. These risk factors are particularly high when the implantation site is located at a point of the body that is difficult to access. Means for simplifying the insertion of implants at implantation sites that are difficult to access are therefore desirable.

SUMMARY OF THE INVENTION

The invention seeks to provide an improved device for the insertion of implants at implantation sites of the body that are difficult to access, or that were previously inaccessible. The device has a surface which at least partially bears a surface structure wherein the coefficient of static friction between the surface structure and an interface within the body is anisotropic. Here, the device could be provided as an implant or as a transportation means for an implant, e.g., a device for implanting an implant.

As an example, it can be difficult to access implantation sites at areas of the body where different structures, such as tissue surfaces, rest alongside or against each another. The invention allows directed displacement of a device between two tissue surfaces lying closely against one another, enabling the insertion and transportation of the device. The device is thus brought to the desired implantation site when the tissue surfaces move relative to one another, either by natural or externally induced movement of the tissue surfaces. The surface structure may be a fixed component of an implant, or may alternatively be part of a carrier arrangement which assists in transporting and/or implanting an implant, and which is formed such that the implant can be separated from the carrier arrangement at the implantation site.

The surface structure is designed to enable a displacement of the device in a controlled direction of displacement. In a preferred version of the invention, the coefficient of static friction between the surface structure and the interface within the body is minimal in a first direction of displacement and is maximal in a second direction of displacement, wherein the first direction of displacement may be opposite the second direction of displacement.

In one version of the invention, the anisotropy of the coefficient of static friction between the surface structure and the interface within the body can be cancelled. This cancellation may occur via a material change to the surface structure, which change may be of a mechanical, thermal, electrical or chemical type. The cancellation can also be initiated by a trigger, which may be mechanical, thermal, electrical or chemical in nature. Alternatively, once the device has reached the desired implantation site, the surface structure can be covered by an additional enveloping substance or structure in order to cancel the anisotropy of the coefficient of static friction.

The surface structure can additionally or alternatively be separated from the device. As an example, the surface structure may be secured on the device by means of a detachable fixing. The fixing may be mechanically detachable, for example, by a thread or other mechanical devices. The device may also have a film on the surface structure, wherein the film can be detached from the device.

The surface structure can additionally or alternatively be formed of a resorbable material. The resorption can be initiated by a mechanical, thermal, electrical or chemical trigger.

The device can have a fixing material, via which the device can be permanently connected to the interface within the body. Examples of fixing materials are tissue adhesives, spring elements, fixing hooks, etc. The fixing material can be activated such that it connects the device to the interface within the body once the surface structure is separated from the device, or once the surface structure has been resorbed.

Alternatively, the cancellation of the anisotropy of the coefficient of static friction can take place by a material that can cancel such anisotropy, with this material being applied to the surface structure. The applied material may be designed to permanently connect the surface structure to the interface within the body.

In a preferred version the surface structure has elements—such as fibers, needles, nubs, lamellae, nibs, spikes or pins—which are oriented at an incline relative to the surface. In the context of the invention, an inclined orientation of the elements relative to the surface is to be understood as meaning an angle of less than 90° for each element relative to the surface of the device.

Suitable materials from which the elements of the surface structure can be fabricated include (for example) titanium; stainless steel; silicone; biocompatible polymers; bioresorbable polymers, such as polymers of glycolic acid or copolymers from glycolide and lactide or polymers from dioxanone; polyether ether ketone (PEEK); bioresorbable magnesium compounds; and resorbable sugar structures, such as mannitol.

The device may also or alternatively include means mounted on the device for controlling a direction of displacement of the device. The means can be used to allow external control of the direction and/or path of displacement during the insertion of the device into the body, and can be provided by (for example) control threads, stylets, or other tethers.

DETAILED DESCRIPTION OF EXEMPLARY VERSIONS OF THE INVENTION

Figure 1:
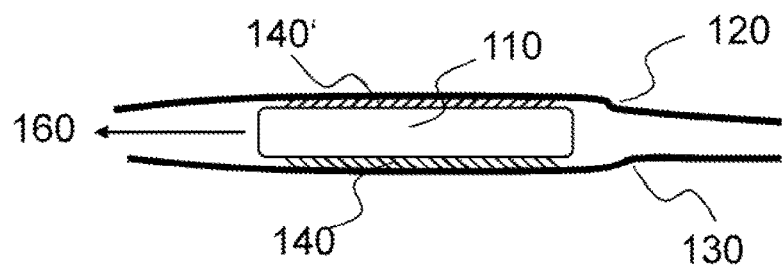
FIG. 1 shows an exemplary version of the device according to the invention.

FIG. 1 schematically illustrates an exemplary version of the invention. A device 110 has a surface structure 140 and 140' located between two tissue surfaces 120 and 130. As a result of the anisotropy of the coefficient of static friction of the surface structure 140 and 140', the device 110 moves/displaces along a predefined direction 160. The device 110 could be (for example) an epicardial cardiac pacemaker, in which case the tissue surfaces 120 and 130 could be the pericardium and epicardium.

Figure 2:
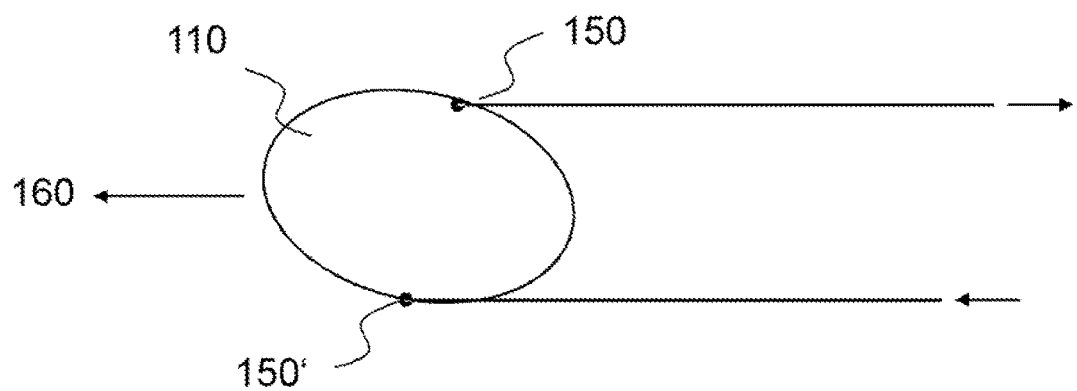
FIG. 2 shows an exemplary version of a device according to the invention with means mounted on the device for controlling the direction of displacement.

FIG. 2 shows an exemplary device 110 wherein means 150 and 150' for controlling the direction of displacement 160 are mounted on the sides of the device 110. The means for direction control may be provided as control threads and/or thin, flexible, and easily deformed stylets. If the device 110 is an epicardial cardiac pacemaker, it may be slid between the pericardium and the epicardium, and may be brought to the desired implantation site using the natural movement of the heart, and/or movement of the pericardium and epicardium relative to one another, and/or by actuation of the means for controlling the displacement direction 150 and 150'.

Figure 3A:
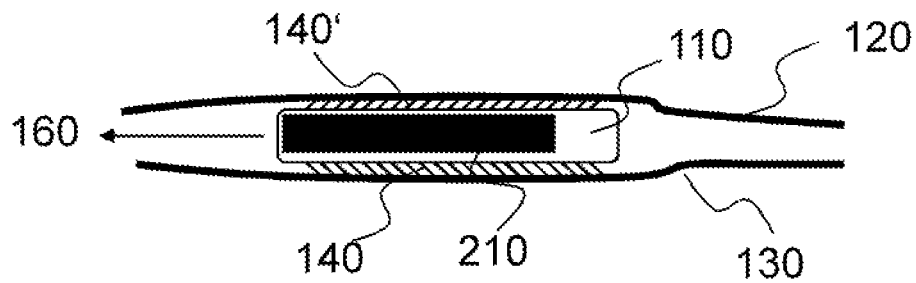
FIG. 3A shows an exemplary version of a device according to the invention as a carrier arrangement in which the surface structure is part of the carrier arrangement.
Figure 3B:
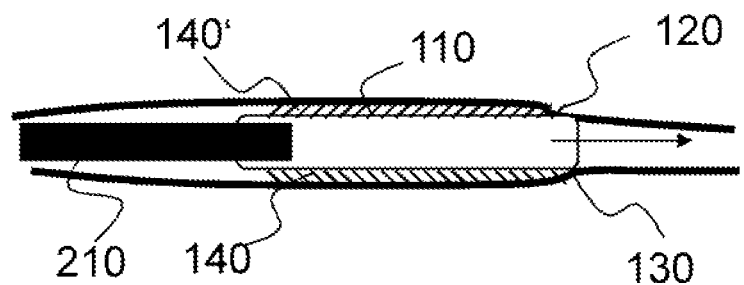
FIG. 3B shows how the implant can be separated from the carrier arrangement at the implantation site.

FIGS. 3A and 3B show an exemplary device 110 formed as a carrier arrangement having surface structure 140 and 140'. The device 100 is located between two tissue surfaces 120 and 130, has a directed (predefined) direction of displacement 160, and is designed to assist with placement of an implant 210. The implant 210 is fixed in or on the device 110, for example by a looped thread. Once the implantation site has been reached, the implant 210 can be separated from the device 110 by releasing the fixation. Alternatively, the fixation may be formed in such a way that the implant 210 can be reconnected to the device 110 prior to a complete release of the fixation, allowing correction of the position of the implant 210.

Figure 4A:
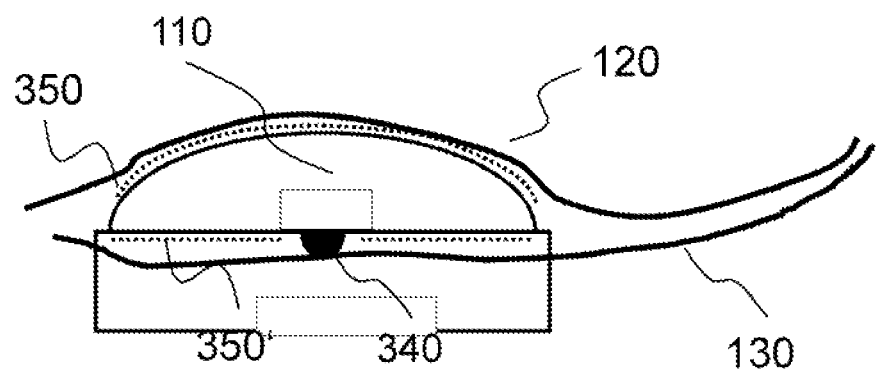
FIG. 4A shows an exemplary version of a device according to the invention wherein the device has a film including the surface structure.
Figure 4B:
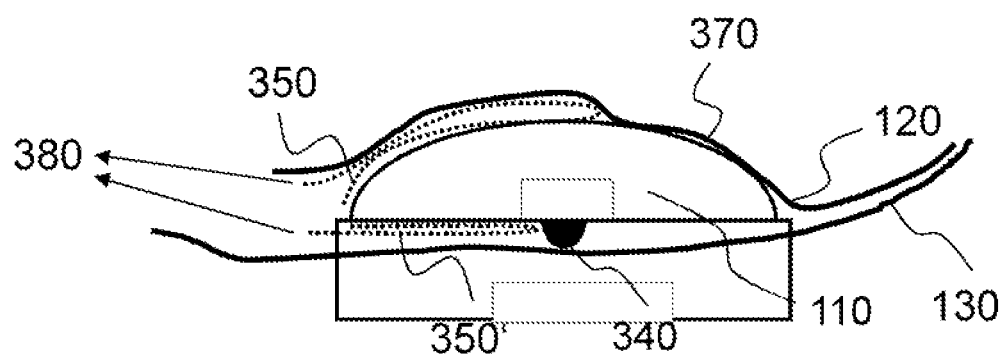
FIG. 4B shows how the film having the surface structure can be detached from the device.

In FIG. 4A, another version of the device 110 is provided as an epicardial cardiac pacemaker located between two tissue surfaces 120 and 130, for example between the epicardium and pericardium. The device 110 has a stimulation pole 340. The surface structure is applied to films 350 and 350' provided on the device 110. As shown in FIG. 4B, once the implantation site has been reached, the films 350 and 350' can be separated from the device 110, for example by being pulled/peeled off in the direction 380. A means 370 for fixing the device 110 to the tissue surfaces 120 and 130, for example a tissue adhesive, might then be activated by removal of the films 350 and 350'.

Figure 5A:
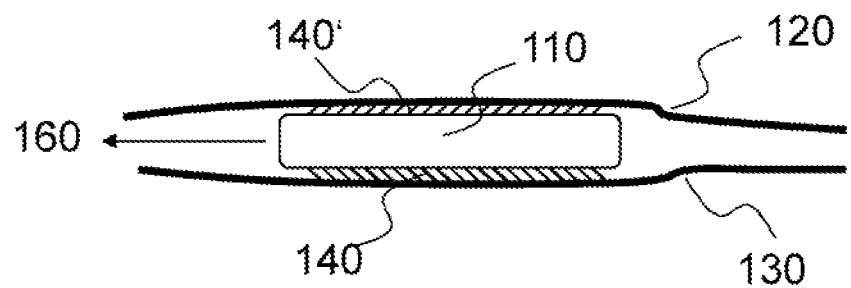
FIG. 5A shows an exemplary version of a device according to the invention in which the anisotropy of the coefficient of static friction of the surface structure can be cancelled.
Figure 5B:
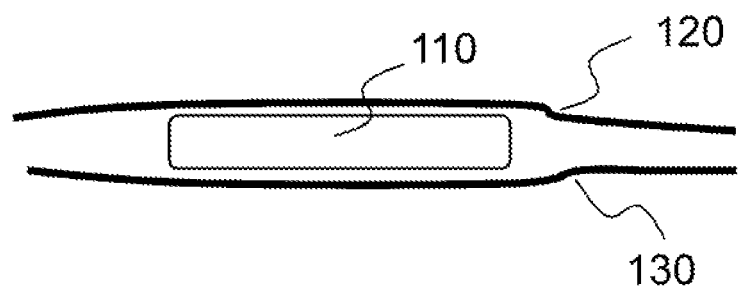
FIG. 5B shows the device once the anisotropy of the coefficient of static friction of the surface structure has been cancelled.
Figure 6A:
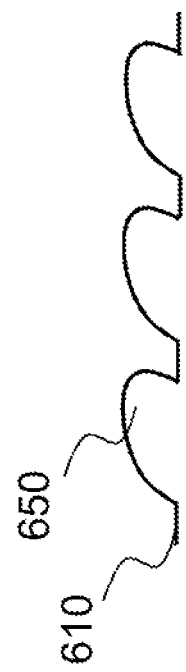
FIGS. 6A-E show possible versions of the elements of the surface structure.
Figure 6B:
Figure 6D:
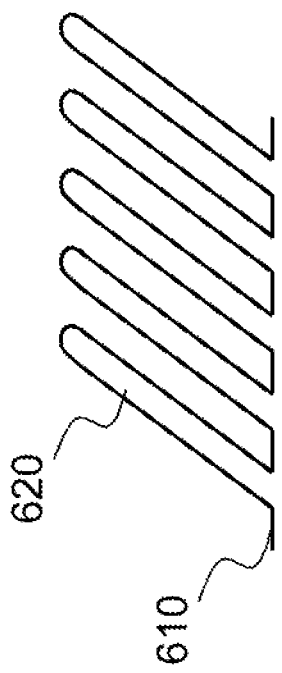
Figure 6E:
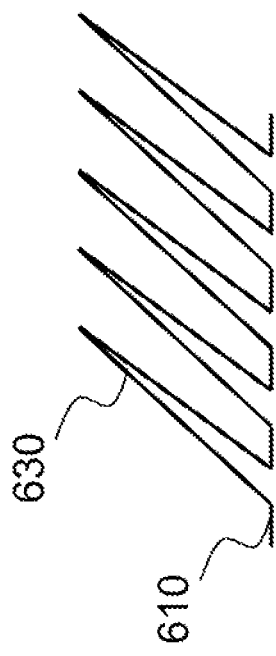
Figure 6C:
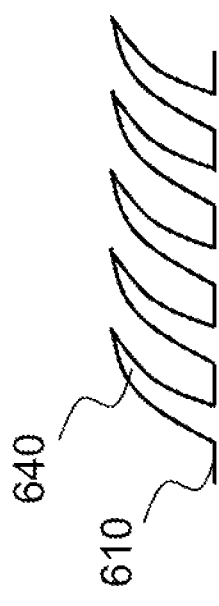

FIGS. 5A and 5B show another version of the invention wherein the anisotropy of the coefficient of static friction of the surface structure 140 and 140' can be cancelled (negated). The device 110, which is located between two tissue surfaces 120 and 130, has a directed displacement direction 160. The anisotropy of the coefficient of static friction of the surface structure 140 and 140' can be cancelled, for example, by a mechanical, thermal, electrical or chemical trigger once the device 110 reaches the desired implantation site. Alternatively or additionally, the surface structure may be formed of a resorbable material, which is absorbed by the tissue after a preferably short period of time.

FIGS. 6A to 6E illustrate exemplary versions of the elements of the surface structure. These may be formed as pins 620, needles 630, bent/flexible nibs or fibers 640, nubs 650, or spikes 660, which are oriented at an incline relative to the surface of the device 610 from which they extend.

Figure 7B:
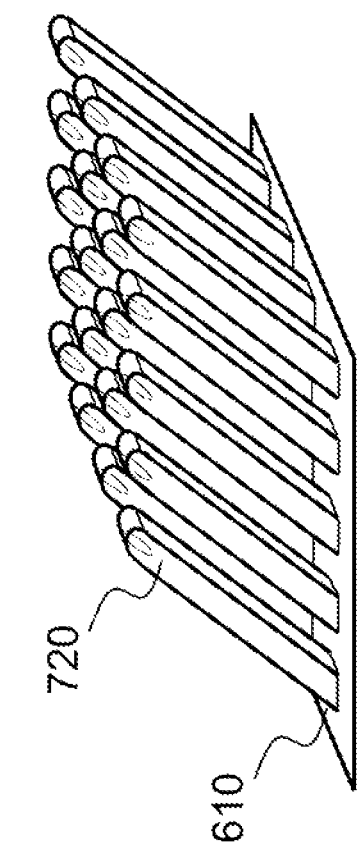
FIGS. 7A-B show possible versions of the elements of the surface structure as individual elements or as a lamellar structure.
Figure 7A:
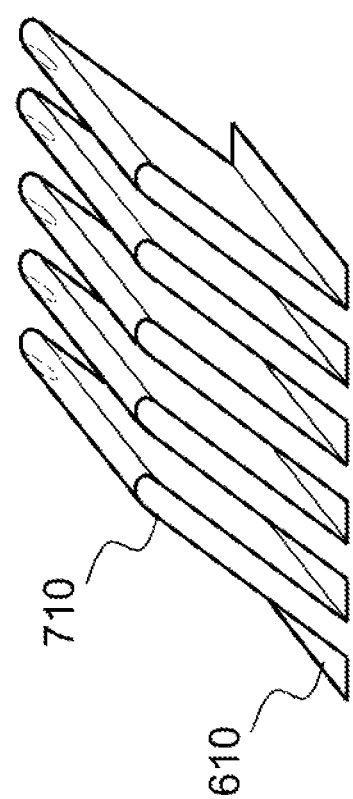

Exemplary three-dimensional versions of the surface structure elements on the device's surface are illustrated in FIGS. 7A and 7B. Here, the elements oriented at an incline relative to the surface of the device 610 are provided in FIG. 7A as fins or lamellae 710, and in FIG. 7B as individual elements 720.

Figure 8A:
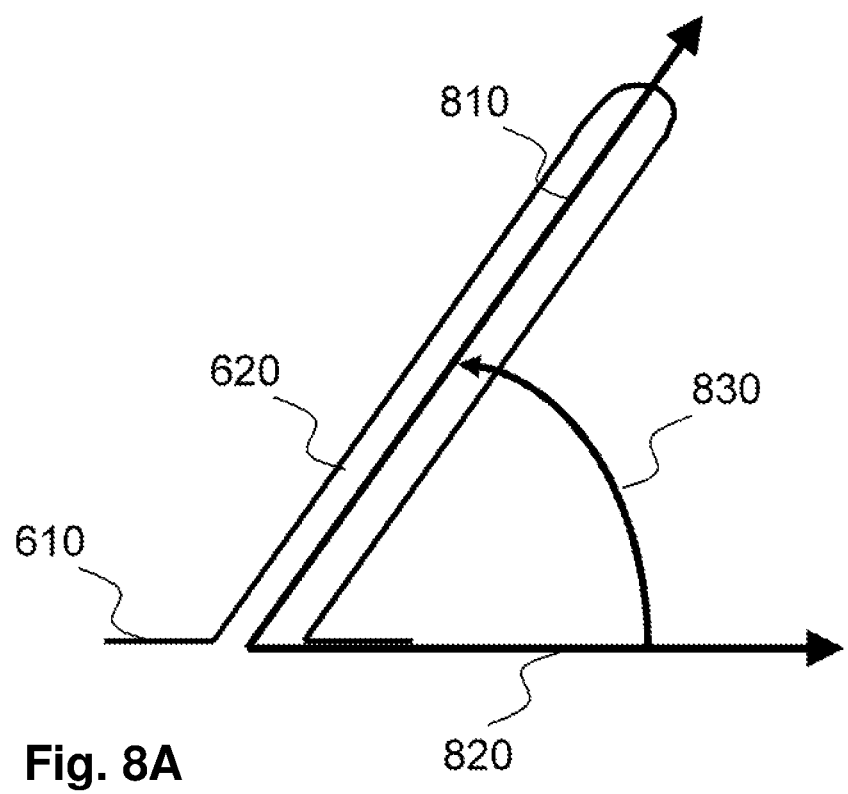
FIGS. 8A-B show angles of an element relative to the surface of the device.
Figure 8B:
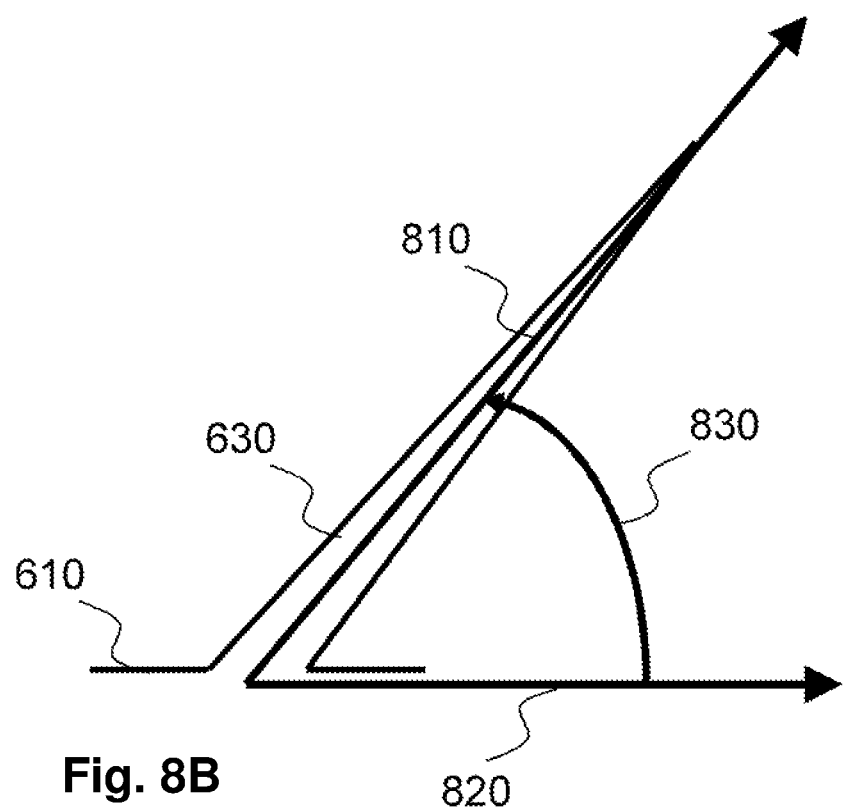

FIG. 8A illustrates the inclined orientation of a surface structure element, here in the form of the pin 620, relative to the surface of the device 610. In this document, such an "inclined orientation" refers to an angle 830 between a vector defined by the orientation of an element 810, and a vector 820 having its starting point at the base of the element 840 and extending parallel or tangentially to the surface of the device 610, wherein the angle 830 is less than 90°. FIG. 8B illustrates the inclined orientation of a surface structure element 630 (a needle) relative to the surface of the device 610.

Figure 9:
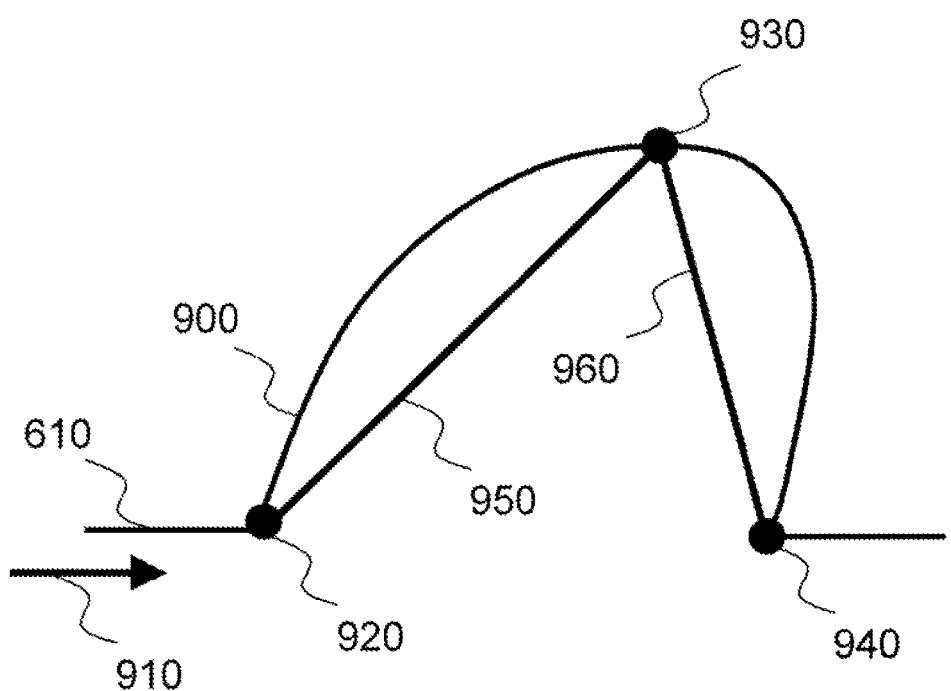
FIG. 9 shows details of the method by which an element of the surface structure is determined to have an "inclined orientation" relative to the surface of the device.

In some cases, the angle of the element with respect to the device surface may be difficult to define because the vectors/legs forming the angle cannot be clearly identified or determined, for example because of the geometry of the elements and/or the device's surface structure. In this case, the meaning of an "inclined orientation" of the elements relative to the device surface is illustrated by the example of FIG. 9, which shows the surface structure element as a nub. A cross-section of the element is shown wherein the cross-sectional plane is spanned by a vector normal to the surface of the device, and by the direction of movement 910 having the smallest coefficient of static friction of the surface structure. The reference numeral 900 represents the edge of the element. The following points are then determined in the following order, following direction 910: first, point 920 on the edge of the element, the point 920 having the smallest distance from the surface of the device; second, point 930 on the edge of the element, the point 930 constituting the first point having the greatest distance from the surface of the device located after point 920; and third, point 940 on the edge of the element, the point 940 being located after point 930 and having the smallest distance from the surface of the device. Two lines 950 and 960 are formed, wherein line 950 extends between points 920 and 930, and line 960 extends between points 930 and 940. The orientation of an element relative to the surface is regarded to be "inclined" when line 950 and line 960 have unequal length.

A preferred potential application for the invention is in conjunction with a cardiac pacemaker implanted in the epicardium (outermost layer of the heart wall), referred to hereinafter as an epicardial cardiac pacemaker. The epicardium lies closely against the pericardium (heart sac), wherein the two tissue surfaces constantly move relative to one another on account of the natural pumping movement of the heart. Using prior art implantation methods, the epicardium is difficult to access as an implantation site. With an implant having the inventive surface structure discussed in this document, the implant can be inserted at an intended implantation site at the epicardium with the assistance of the natural movement of the heart, and the movement of epicardium and pericardium relative to one another. The implant is firstly placed at a suitable point between the epicardium and pericardium, such that the surface structure is in contact with at least one of the tissue layers. Due to the surface structure's anisotropic coefficient of static friction and the movement of both tissue layers relative to one another, the implant is moved along the two interfaces in a direction that has a low static friction with respect to the surface structure.

The invention is applicable to different implants, whether active or passive, and whether temporary or permanent, such as cardiac stimulators, neurostimulators, pulse generators, all types of sensors and sensor leads, drug carriers, radionuclide carriers, medical markers (such as X-ray markers), temporary and permanent catheters, and suture and closure systems.

Apart from the implantation sites discussed above, the invention can be used at implantation sites such as sub- or intrameningeal or intrapleural locations, positions or gaps between organs (for example the liver, kidneys, stomach, diaphragm), and/or within lumen such as the urethra and blood vessels. A naturally occurring movement of an interface within the body does not necessarily have to be provided or used for the insertion/placement of the device, and can alternatively or additionally be externally induced.

Exemplary versions of the invention have been described above, and the invention is not limited to these exemplary versions, and rather is limited only by the claims set out below. Thus, the invention encompasses all different versions that fall literally or equivalently within the scope of these claims.

What is claimed is:

1. A device (110) for insertion into a human or animal body, the device including an outer surface (610) at least partially bearing a surface structure (140, 140'), wherein the coefficient of static friction between the surface structure (140, 140') and an interface within the body is anisotropic, the device (110) further including control means mounted on the outer surface (610) for controlling a direction of displacement (150, 150') of the device (110), the control means having a length extending from the surface (610) which is greater than a maximum diameter of the device, the maximum diameter being measured between the furthermost opposing points on the outer surface (610) of the device.

2. The device (110) of claim 1 wherein the device is defined by one of:
   a. an implant, or
   b. a carrier device configured to transport an implant within a body.

3. The device (110) of claim 1 wherein the coefficient of static friction between the surface structure (140, 140') and the interface within the body is:
   a. minimal in a first direction of displacement (160), and
   b. maximal in a second direction of displacement opposite the second direction of displacement.

4. The device (110) of claim 1 wherein the coefficient of static friction between the surface structure (140, 140') and the interface within the body is:
   a. minimal in a first direction of displacement (160), and
   b. greater than the minimal coefficient of static friction in directions of displacement oriented at greater than 90 degrees from the first direction of displacement.

5. The device (110) of claim 1 wherein the anisotropy of the coefficient of static friction can be cancelled without deformation of the surface (610) of the device (110).

6. The device (110) of claim 1 wherein the surface structure (140, 140') can be separated from the device (110).

7. The device (110) of claim 1 wherein the surface structure (140, 140') is defined by a resorbable material.

8. The device (110) of claim 1 further including a fixing material (370) configured to permanently connect the device (110) to the interface within the body.

9. The device (110) of claim 1 in combination with a material configured to cancel the anisotropy of the coefficient of static friction when applied to the surface structure (140, 140').

10. The device (110) of claim 9 wherein the material configured to cancel the anisotropy of the coefficient of static friction is further configured to permanently connect the surface structure (140, 140') to the interface within the body.

11. The device (110) of claim 1 wherein the surface structure (140, 140') includes elements (620, 630, 640, 650, 660, 710, 720) oriented at an incline relative to the surface.

12. The device (110) of claim 10 wherein the elements (620, 630, 640, 650, 660, 710, 720) are defined by one or more of:
   a. fibers,
   b. needles,
   c. nubs,
   d. lamellae,
   e. nibs,
   f. spikes, and
   g. pins.

13. The device (110) of claim 1 further including a tether extending from the device (110), the tether being configured to control a direction of displacement (150, 1505 of the device (110).

14. The device (110) of claim 1 wherein the surface structure (140, 140') is situated on the surface (610) on at least opposite sides of the circumference of the device (110).

15. A device (110) for insertion into a human or animal body wherein:
   a. the device is defined by one of:
      (1) an implant, or (2) a carrier device configured to transport an implant within a body;

b. the device includes a surface (610) having elements (620, 630, 640, 650, 660, 710, 720) extending therefrom at an incline relative to the surface, the elements:

(1) providing an anisotropic coefficient of static friction between the surface structure (140, 140') and an interface within the body, and (2) being configured to cancel the anisotropic coefficient of static friction after insertion within the body, without deformation of the device's surface.

16. The device (110) of claim 15 wherein the elements (620, 630, 640, 650, 660, 710, 720) are defined by a resorbable material.

17. A device (110) for insertion into a human or animal body wherein:

a. the device is defined by one of:

(1) an implant, or (2) a carrier device configured to transport an implant within a body;

b. the device includes a surface (610) having elements (620, 630, 640, 650, 660, 710, 720) extending therefrom at an incline relative to the surface, the elements:

(1) providing a coefficient of static friction between the surface structure (140, 140') and an interface within the body wherein the coefficient is:

(a) minimal in a first direction of displacement (160) of the device (110) with respect to the interface, and (b) greater than the minimal coefficient of static friction in directions of displacement oriented at greater than 90 degrees from the first direction of displacement; and (2) being removable from the device (110).

18. The device (110) of claim 17 wherein the elements (620, 630, 640, 650, 660, 710, 720) are resorbable within the body.

19. The device (110) of claim 17 wherein the surface (610) is peelable from the device (110).

\* \* \* \* \*